United States Patent [19]

Anderson

[11] 4,202,058
[45] May 13, 1980

[54] FEMALE URINAL

[76] Inventor: Robert W. Anderson, 1765 S. 79th East Ave., Tulsa, Okla. 74112

[21] Appl. No.: 956,106

[22] Filed: Oct. 31, 1978

[51] Int. Cl.² ............................................. A61G 9/00
[52] U.S. Cl. .................................................... 4/144.3
[58] Field of Search .................. 4/144.3, 113.1, 144.4, 4/144.2, 311

[56] References Cited

U.S. PATENT DOCUMENTS

| | | | |
|---|---|---|---|
| 301,219 | 7/1884 | Davis | 4/144.1 |
| 3,114,916 | 12/1963 | Hadley | 4/144.3 |
| 3,335,714 | 8/1967 | Giesy | 4/144.3 |
| 4,117,845 | 10/1978 | Brown | 4/144.1 |
| 4,121,306 | 10/1978 | Bringman et al. | 4/144.3 |

*Primary Examiner*—Lenard A. Footland
*Attorney, Agent, or Firm*—Fleit & Jacobson

[57] ABSTRACT

A urinal for supine use. The urinal has a flexible inner liner cooperating with a rigid outer shell to define a generally oval-shaped receiving chamber. Edge portions of the inner liner protrude beyond the outer shell and are deformable to sealingly engage body parts of an intended user. A pump communicates through a duct section with the receiving chamber to evacuate collected liquid from the receiving chamber.

4 Claims, 6 Drawing Figures

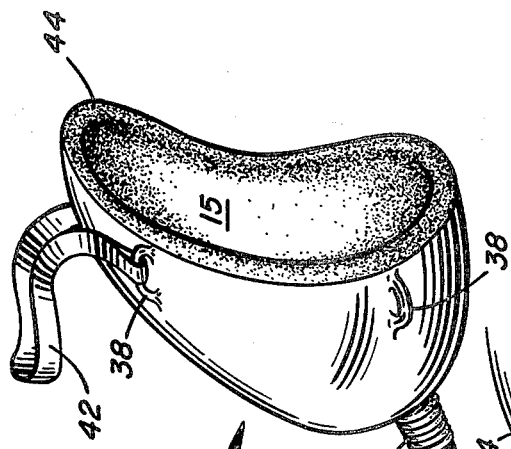
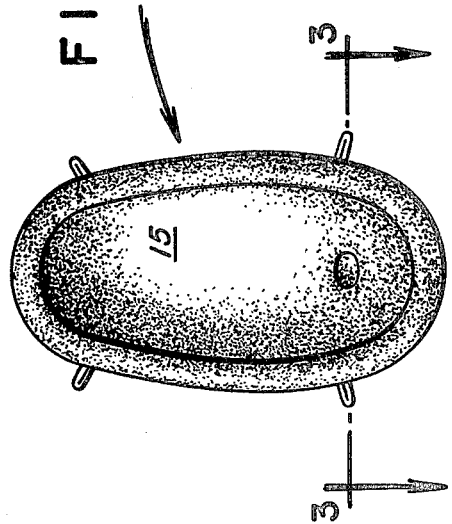
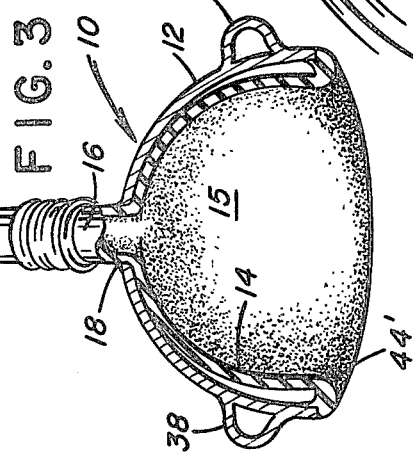
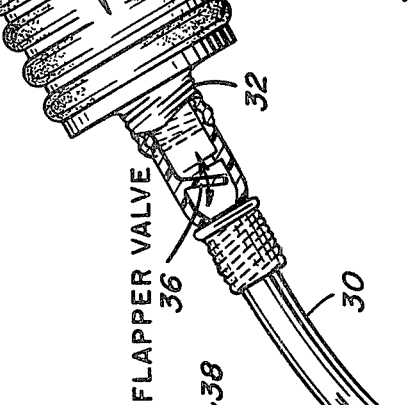
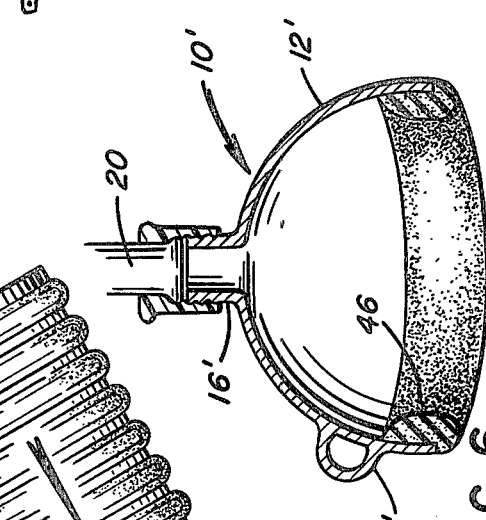

FEMALE URINAL

BACKGROUND OF THE INVENTION

1. Field of the Invention

This invention relates to equipment useful at the sick bed, and relates in particular to improvements in female urinals intended for supine use.

2. Description of the Prior Art

The present invention solves in a satisfactory manner the problem of providing a female urinal for use where the patient is in supine position and substantially immobile. Numerous types of such devices are previously known. Examples of such prior art devices are found in U.S. Pat. No. 587,803, entitled "Portable Urinal"; U.S. Pat. No. 1,440,765, entitled "Urinal"; U.S. Pat. No. 2,382,276, entitled "Female Urinal"; and U.S. Pat. No. 3,161,891, entitled "Portable Urine Specimen Collecting Device".

SUMMARY OF THE INVENTION

The present invention provides a urinal specially adapted for female use, although the urinal or a modification thereof can be satisfactorily used by a male.

The urinal of the present invention is held in a position ready for use by the user or by another person. Alternatively, the urinal can be strapped to the user and left in position. The urinal has a receiving part or cup with a deformable outer edge that readily yields and forms to the area surrounding the vulva of a user. The outer edge, when the urinal is applied, automatically forms a sealing engagement with the body parts engaged so the leakage does not occur. Urine collected in the receiving portion of the urinal leaves the receiving portion via an outlet connected to flexible tubing. The tubing is connected to a pump so that the urine can be removed from the receiving cup without having to elevate the cup. This feature of the present invention greatly reduces the risk of undesirable leakage.

Two embodiments of the present invention will be described in greater detail hereinafter. The first embodiment has a rigid outer shell with a soft, pliant inner shell affixed thererto. The outer shell contains an opening for a piece of tubing or duct section molded integrally with the inner shell. The duct section provides fluid communication between the inner shell and flexible tubing connected to the duct. The flexible tubing is connected to a pump which evacuates the receiving cup and transfers the evacuated urine to a storage receptacle or container.

The second embodiment utilizes a rigid outer shell to form a receiving cup. One end of the shell has a molded outlet defining a duct section connectable to flexible tubing. The other end of the cup is open and has a generally oval shape designed to readily conform to the area surrounding the vulva of a user. A resilient, deformable material is connected to and extends outwardly from edge portions of the open end to provide sealing engagement between the cup and engaged body parts of a user.

The invention, and its objects and advantages, will become more apparent in the detailed description of the preferred embodiments presented below.

BRIEF DESCRIPTION OF THE DRAWINGS

In the detailed description of the preferred embodiments of the invention presented below, reference is made to the accompanying drawings, in which:

FIG. 1 is a perspective of one embodiment of the present invention;

FIG. 2 is a plan view of the front receiving end of the embodiment of FIG. 1;

FIG. 3 is a cross-sectional view along line 3—3 of FIG. 2;

FIG. 4 a is side elevation, partially in section, of a pump usable with the embodiment of FIG. 1;

FIG. 5 is a rear plan view of a modification of FIG. 1; and

FIG. 6 is a sectional view, similar to FIG. 3, illustrating another embodiment of the present invention.

DESCRIPTION OF THE PREFERRED EMBODIMENTS

Because urinals are well known, the present description will be directed in particular to elements forming part of, or cooperating more directly with, the present invention. Elements not specifically shown or described herein are understood to be selectable from those known in the art.

Referring now to the drawings, and to FIGS. 1 to 3 in particaular, one embodiment of the present invention is illustrated and will be described in connection with a female urinal, generally designated 10.

The urinal 10 has a rigid outer shell 12, preferably oval-shaped, and a flexible inner shell 14 positionable within the shell 12 to define a receiving chamber 15. The inner shell 14 has a duct section 16 which extends through an aperture or opening 18 formed in the outer shell 12 when the inner shell 14 is connected to the outer shell 12. The connection between the inner and outer shells is accomplished in any suitable manner, for instance, by ultrasonic welding, by gluing, by heat sealing.

A section of flexible tubing 20 has a first end 22 connectable to the duct section 16 and a second end 24 connectable to the inlet end 26 of a pump 28, as illustrated in FIG. 4. The connections should be threaded to preventing pulling apart. A second piece of flexible tubing 30 extends from the outlet end 32 of the pump to a storage container (not shown). The pump includes one-way inlet and outlet valves 34 and 36, respectively. Valve construction allows most of the voided fluid to flow freely. Preferably, the pump is a plastic gasoline-type bellows pump.

The outer surface of the outer shell 12 includes four or more protrusions 38 which provide brackets for connecting to the outer shell belts 40, as illustrated in FIG. 5, and/or a hanger 42, as illustrated in FIG. 1. The belts 40, which are preferably adjustable elastic hip straps, make it possible to hold the urinal 10 in place for a patient with incontinence. The hanger 42 makes it possible to conveniently hang the urinal 10, for instance, on a side rail of a hospital bed.

The inner shell 14 has flexible, deformable edge portions 44 which extend beyond the edges of shell 12 to provide efficient sealing engagement between the urinal and engaged body parts of a user. Preferably, edge portions 44 are ribbed to improve sealing.

Referring now to FIG. 6, another embodiment of the urinal of the present invention is illustrated. Since this embodiment is quite similar to the previously described embodiment, the same reference numerals, with primes attached, have been used to identify the same or similar components.

The urinal illustrated in FIG. 6, which is generally designated 10′, has a rigid outer shell 12′ and a flexible inner liner 46 attached to and extending outwardly from edge portions of the shell 12′. The liner 46, which is preferably deformable, provides an efficient sealing engagement between the urinal 10′ and the engaged body parts of an intended user. A duct section 16′ extends forward at approximately 45° from the outer shell 12′ to enable connection of flexible tubing 20 to the urinal 10′. Protrusions 38′ are provided on the exterior surface of the outer shell 12′ to enable selective connection of belts 40 and hangar 42 to the shell.

Considering now the use of the urinal 10, the urinal is held sealingly engaged with body parts of an intended user by the intended user, by another person, or by the belts 40. After or during use, urine collected in the receiving chamber 15 is evacuated from the shell by operating the pump 28. Operation of the pump 28 prior to removal of the urinal 10 greatly reduces the possibility of undesirable leakage during removal of the urinal.

The embodiment illustrated in FIG. 6 functions in the same manner as the embodiment illustrated in FIG. 1. End portions of liner 46, which are similar to the edge region 44 of inner shell 14, are deformed against the body parts of a user to ensure sealing engagement between the urinal and a user. After or during use, urine collected within the receiving chamber defined by the outer shell 12′ is evacuated from the chamber by operation of the pump 28.

Preferably, both of the described embodiments of the present invention are molded from a plastic material that can be readily sterilized. After a period of use of the urinal, the flexible tubing is removed from the urinal to allow such sterilization.

As an aid to understanding the present invention, some representative dimensions of component members of the urinal will be set forth. First, the open end of the oval-shaped receiving chamber has a major axis approximately 4 inches long and a minor axis approximately 2 inches long. The inner shell or liner extends beyond the edge of the outer shell for a distance of approximately ¼ inch. The flexible tubing connecting the duct section with the pump has a length of approximately 12 inches. It will be appreciated that the foregoing are only representative dimensions and that other dimensions, depending on the needs of a contemplated user, are usable in the urinal of the present invention.

While the present invention has been discussed in connection with a urinal intended for female use, it will be readily appreciated that a male can also use the urinal.

The present invention has been described in detail with particular reference to preferred embodiments thereof, but it will be understood that variations and modifications can be effected within the spirit and scope of the invention.

I claim:

1. A urinal for supine or reclining female use comprising:
   a rigid outer shell defining an open chamber, edge portions of said outer shell defining a generally oval-shaped opening for the chamber;
   a flexible inner shell defining a receiving chamber positionable within said outer shell in such manner that edge portions of said inner shell protrude outwardly beyond edge portions of said outer shell, said protruding edge portions being deformable and said generally oval shape being such that said urinal is sealingly engaged with body parts of an intended user when the urinal is pressed against the body parts;
   said outer shell including an aperture defined therein and said inner shell including a duct section that communicates with the receiving chamber and extends through said aperture when said inner shell is positioned in said outer shell;
   manually powered pump means connectable to said duct section for evacuating urine from said receiving chamber after or during use of said urinal;
   a first tubing section for connecting an inlet of said pump means to said duct section;
   one-way valve means, positioned between the pump inlet and said duct section for limiting fluid flow to a direction extending from said duct section to said pump means; and
   a second tubing section connected to an outlet of said pump means for carrying urine away from said pump means; and further comprising
   a first pair of brackets positioned on opposite sides of upper portions of said outer shell;
   a second pair of brackets positioned on opposite sides of lower portions of said outer shell;
   adjustable hip straps connected to said first and second pairs of brackets for holding said urinal on a user in a position ready for use; and
   a hanger connected to said outer shell for suspending said urinal from a support.

2. A urinal according to claim 1 wherein said inner shell is sealed to said outer shell prior to use of said urinal.

3. A urinal according to claim 1, wherein said pump means comprises a bellows pump formed of plastic material, wherein said one-way valve means comprises a flapper valve positioned between the end of said first tubing section closest to said pump means and an inlet to said bellows pump, and wherein said urinal further comprises a second flapper valve positioned between an outlet from said bellows pump and the second tubing section for limiting fluid flow to a direction extending from said pump means to said second tubing section.

4. A urinal for supine or reclining female use comprising:
   a rigid outer shell defining an open chamber, edge portions of said outer shell defining an opening having a generally oval shape;
   a flexible inner liner forming a collar connected to edge portions of said outer shell in such manner that outer edge portions of said inner liner protrude from said chamber beyond edge portions of said outer shell, said inner liner cooperating with said outer shell to define a receiving chamber, said protruding edge portions being deformable and said generally oval shape being such that said urinal is sealingly engaged with body parts of an intended user when the urinal is pressed against the body parts;
   a duct section extending from said outer shell and in fluid communication with said receiving chamber;
   pump means connectable to said duct section for evacuating urine from said receiving chamber after or during use or said urinal;
   a tubing section for connecting an inlet of said pump means to said duct section; and one-way valve means positioned between the pump inlet and said duct section for limiting fluid flow to a direction extending from said duct section to said pump means; and further comprising a first pair of brackets positioned on opposite sides of upper portions of said outer shell;

a second pair of brackets positioned on opposite sides of lower portions of said outer shell;

adjustable hip straps connected to said first and second pairs of brackets for holding said urinal on a user in a position ready for use; and a hanger connected to said outer shell for suspending said urinal from a support,

* * * * *